(12) United States Patent
Kraemer et al.

(10) Patent No.: US 7,133,716 B2
(45) Date of Patent: Nov. 7, 2006

(54) DETERMINING THE HYDRATION STATUS OF A PATIENT

(75) Inventors: Matthias Kraemer, Friedrichsdorf (DE); Paul Chamney, Herts (GB)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 234 days.

(21) Appl. No.: 10/497,172

(22) PCT Filed: Dec. 12, 2001

(86) PCT No.: PCT/EP01/14594

§ 371 (c)(1),
(2), (4) Date: Jun. 9, 2004

(87) PCT Pub. No.: WO03/053239

PCT Pub. Date: Jul. 3, 2003

(65) Prior Publication Data

US 2005/0039763 A1    Feb. 24, 2005

(51) Int. Cl.
*A61B 5/05* (2006.01)

(52) U.S. Cl. .................................................. 600/547

(58) Field of Classification Search ................ 600/547, 600/506, 399, 536, 442
See application file for complete search history.

(56) References Cited

U.S. PATENT DOCUMENTS

| | | | | |
|---|---|---|---|---|
| 4,793,362 A | * | 12/1988 | Tedner | 600/547 |
| 5,086,781 A | * | 2/1992 | Bookspan | 600/547 |
| 5,449,000 A | * | 9/1995 | Libke et al. | 600/547 |
| 5,788,643 A | * | 8/1998 | Feldman | 600/506 |
| 6,208,890 B1 | * | 3/2001 | Sarrazin et al. | 600/547 |
| 6,228,033 B1 | * | 5/2001 | Koobi et al. | 600/483 |
| 6,246,894 B1 | * | 6/2001 | Steuer et al. | 600/322 |
| 6,587,715 B1 | * | 7/2003 | Singer | 600/547 |
| 6,615,077 B1 | * | 9/2003 | Zhu et al. | 600/547 |
| 2002/0112898 A1 | * | 8/2002 | Honda et al. | 177/245 |
| 2004/0064063 A1 | * | 4/2004 | Chamney | 600/547 |

FOREIGN PATENT DOCUMENTS

| | | |
|---|---|---|
| GB | 2 304 414 A | 3/1997 |
| JP | 10-014899 | * 1/1998 |
| JP | 2001-321350 | * 11/2001 |
| WO | WO92/19153 | 11/1992 |

OTHER PUBLICATIONS

DuBois, D., et al., "A Formula to Estimate the Approximate Surface Area If Height and Weight Be Known", The Archives of Internal Medicine, pp. 863-871, 1916.

(Continued)

*Primary Examiner*—Max F. Hindenburg
*Assistant Examiner*—Kristin D Rogers
(74) *Attorney, Agent, or Firm*—Jacobson Holman PLLC (57) ABSTRACT

A device and method are provided for determining the volume $ECV_{hydr}(t)$ of a body compartment of a patient at a time t by conducting measurements at the time t of the patient to determine at least one anthropometric measure $X(t)$, the extracellular water volume $ECV(t)$, and the intracellular water volume $ICV(t)$ of the patient. The extracellular water volume $ECV_{basic}(t)$ of a first compartment with weight $W_{basic}(t)$ of the patient at the time t is derived by using $X(t)$, the extracellular water volume $ECV_{sec}(t)$ of a second compartment of the patient at the time t is derived by using $ICV(t)$, and $ECV_{hydr}(t)$ as the extracellular water volume of a third compartment of the patient is derived with weight $W_{hydr}(t)$. The extracellular volume $ECV_{hydr}(t)$ is a measure for the hydration status of the patient.

55 Claims, 6 Drawing Sheets

OTHER PUBLICATIONS

Skelton, H., "The Storage of Water By Various Tissues of the Body", The Archives of Internal Medicine, vol. 40, pp. 140-152, 1972.

Human Body Composition, "Estimation of Muscle Mass", pp. 118-120, 1996.

Rico, H., et al., "Sex Differences in the Acquisition of Total Bone Mineral . . . ," Calcified Tissue Int., pp. 251-254, 1992.

Weiss, C., et al., "Funktionen des Blutes", Chapter 18 in Physiologie des Menschen, (Schmidt et al., eds.), pp. 422-460, 1987. (Abstract only).

Witzeleb, E., et al., "Funktionen des Gefäβsystems", Chapter 20 in Physiologie des Menschen, (Schmidt et al., eds.), pp. 505-571, 1987. (Abstract only).

* cited by examiner

| component i | mass fraction Female | mass fraction Male | parameter |
|---|---|---|---|
| | | | $k_{basic,i}$ |
| bones | 0.126 | 0.159 | $k_{skeleton}$ |
| organs | 0.078 | 0.078 | $k_{organ}$ |
| blood | 23.0 ml/kg | 23.0 ml/kg | $k_{blood,av}$ |
| blood | 123.5 ml/kg | 123.5 ml/kg | $k_{blood,muscle}$ |
| skin | 0.18 | 0.18 | $k_{skin}$ |

Figure 6

| component i | parameter $\lambda$ | water content per component mass | ECV/TBV or ICV/TBV ratio | value |
|---|---|---|---|---|
| Skeleton | $\lambda_{ECV,skelet}$ | 22% | 0.44 | 0.096 litre/kg |
| Organs | $\lambda_{ECV,organs}$ | 76.2% | 0.44 | 0.335 litre/kg |
| Blood | $\lambda_{ECV,blood}$ | 79.1%-86.2% | 0.563 – 0.820 | 0.445-0.707 litre/kg |
| Skin | $\lambda_{ECV,skin}$ | 72% | 0.44 | 0.317 litre/kg |
| Skeleton | $\lambda_{ICV,skelet}$ | 22% | 0.56 | 0.127 litre/kg |
| Organs | $\lambda_{ICV,organs}$ | 76.2 | 0.56 | 0.427 litre/kg |
| Blood | $\lambda_{ICV,blood}$ | 79.1%-86.2% | 0.180 – 0.438 | 0.155-0.346 litre/kg |
| Skin | $\lambda_{ICV,skin}$ | 72% | 0.56 | 0.403 litre/kg |

DETERMINING THE HYDRATION STATUS OF A PATIENT

This is a nationalization of PCT/EP01/14594 filed Dec. 12, 2001 and published in English.

BACKGROUND OF THE INVENTION

1. Field of the Invention

The invention relates to the field of monitoring the hydration and/or nutrition status of a patient.

2. Description of the Related Art

The kidneys carry out several functions for maintaining the health of a human body. First, they control the fluid balance by separating any excess fluid from the patient's blood volume. Second, they serve to purify the blood from any waste substances like urea or creatinine. Last not least they also control the levels of certain substances in the blood like electrolytes in order to ensure a healthy and necessary concentration level.

In case of renal failure ingested fluid accumulates in body tissues and the vascular system causing increased stress on the circulatory system. This surplus fluid has to be removed during a dialysis treatment by ultrafiltration of the blood. If insufficient fluid is removed the long term consequences can be severe, leading to high blood pressure and cardiac failure. Cardiac failure itself is many times more likely to occur in dialysis patients and it is thought that states of fluid overload are one of the major contributing factors. Removal of too much fluid is also dangerous since the dialysis patient becomes dehydrated and this invariably leads to hypotension.

The dry weight (for the sake of simplicity the words "weight" and "mass" shall be used synonymously throughout this patent application document—which is usual practise in the medical field anyway) defines the weight of a patient that would be achieved if the kidneys were working normally. In other words this represents the optimal target weight (or fluid status) which should be achieved in order to minimise cardiovascular risk. Dry weight has always been an elusive problem in routine clinical practise due to lack of quantitative methods for its assessment. Currently the dry weight problem is approached using indirect indicators like e.g. blood pressure, echocardiographic investigations and subjective information such as X-rays. Furthermore it has been particularly difficult to define a set of conditions which are universally accepted as the dry weight standard.

A promising method to derive the fluid status of a patient involves the use of bioimpedance measurements. A small alternating current is applied to two or more electrodes which are attached to a patient and the corresponding electric potential difference is measured. The various fluid compartments of a human body contribute differently to the measured signals. The use of multiple frequencies allows the intracellular water (ICV) and extracellular water (ECV) volumes to be determined. An example of such a device is described in the international patent application WO 92/19153. However, this document discloses no method regarding how the dry weight of the particular patient can be derived.

The U.S. Pat. No. 5,449,000 describes a bioimpedance system also using multiple frequencies to determine ECV and ICV. Furthermore certain population dependent data are taken for using and choosing so-called population prediction formulas. The body composition is then analysed by using these formulas and with the help of segmental bioimpedance signals. This document also lacks a disclosure of a method how the dry weight may be derived.

Hence there is a need for a non-invasive, accurate and easy to use method for dry weight assessment which nevertheless takes into account individual variations without grossly limiting the analysis to certain populations. This method would be of major benefit to the management of dialysis patients and could significantly reduce hospitalisation costs in the long term. There is also a need for an easy to carry out method to assess the body composition of a patient in a more general manner, providing additional insight into the nutrition and training status.

SUMMARY OF THE INVENTION

It is an object of this invention to provide such a method.

According to the invention this problem is solved by a method for determining a body compartment $ECV_{hydr}(t)$ of a patient at a time t comprising the steps of determining at least one anthropometric measure $X(t)$ of the patient at the time t, determining the extracellular water volume $ECV(t)$ of the patient at the time t, determining the intracellular water volume $ICV(t)$ of the patient at the time t, deriving the extracellular water volume $ECV_{basic}(t)$ of a first compartment with weight $W_{basic}(t)$ of the patient at the time t by using $X(t)$, deriving the extracellular water volume $ECV_{sec}(t)$ of a second compartment of the patient at the time t by using $ICV(t)$, and deriving the volume $ECV_{hydr}(t)$ as the extracellular water volume of a third compartment of the patient with weight $W_{hydr}(t)$ by using the equation $$ECV_{hydr}(t) = ECV(t) - ECV_{basic}(t) - ECV_{sec}(t) \qquad (1).$$

The invention provides for an easy and straight forward method to directly address the dry weight management of a patient. As will be outlined below this is possible because the invention is based on the observation that some body compartments only vary in a very predictable manner from one individual to another whereas other compartments show a much larger variability which may be-addressed only by appropriate measurements. By transferring this observation to an analysis of the body compartments with respect to their ECV and ICV contributions the method according to the invention is found. The hydration status maybe analysed entirely by the status of a single body compartment which was appropriately separated from the other compartments which correspond to the status of individuals which are not mal-hydrated. For these individuals the single body compartment which is representing the hydration status would have a negligible volume. For over-hydrated individuals like patients with renal failure this body compartment has a positive volume. For de-hydrated individuals like patients suffering from gross fluid loss or too low fluid intake it is negative.

The variability of the first compartment of the patient is mainly dependent on the anthropometric measure $X(t)$. Anthropometric measures shall comprise all geometric dimensions/sizes and/or weight data of the patient which relate to the weight $W_{basic}(t)$ of the first compartment. An example for $X(t)$ is the height $H(t)$ of the patient.

The volume $ECV_{sec}(t)$ of the second compartment is characterized by a variability in cell mass that can appropriately be described by an ICV measurement (or a measurement correlated with it). One such compartment is the compartment of muscle tissue with weight $W_{muscle}(t)$ and extracellular water volume $ECV_{muscle}(t)$.

Once the hydration status of the patient is derived other information may be derived in further embodiments of the invention. According to one such embodiment the weight $W_{sec}(t)$ of the second compartment and the weight $W_{fat}(t)$ of a fourth compartment of the patient at the time t, the latter representing the fat mass, are also derived. Hence the invention provides for an easy and convenient method to also assess the nutrition and training status of the patient.

In a preferred embodiment of the, invention ECV(t) and ICV(t) are derived by a bioimpedance measurement. The bioimpedance measurement may be a whole body or a segmental measurement. The bioimpedance measurement may be performed at a single frequency, at a small number of frequencies (typically 2–4), or in multi-frequency mode, the latter being the preferred embodiment since this mode should allow the most precise determination of ECV(t) and ICV(t).

It is also an object of the invention to provide a device for a non-invasive, accurate and easy to use dry weight and/or body compartment assessment. The invention therefore also concerns a device for carrying out the method according to the invention comprising a microprocessor unit which in turn comprises a microprocessor program storage unit, an input unit to enable entering values of ECV(t), ICV(t) and X(t), a computer storage unit for storing the ECV(t), ICV(t) and X(t) values, wherein the microprocessor program storage unit comprises a program for deriving the extracellular water volume $ECV_{hydr}(t)$ by deriving the extracellular water volume $ECV_{basic}(t)$ of the first compartment with weight $W_{basic}(t)$ of the patient at the time t by using the value(s) of X(t), by deriving the volume $ECV_{sec}(t)$ of the second compartment with weight $W_{sec}(t)$ by using the value of ICV(t) and by deriving the volume $ECV_{hydr}(t)$ as the extracellular water volume of the third compartment of the patient with weight $W_{hydr}(t)$ by using equation (1).

In a preferred embodiment of the invention the device further comprises means for determining the ECV(t) and ICV(t) values. The means for determining these values may be a bioimpedance device, applied in a whole body or segmental measurement mode.

The input unit may be a manual user interface such as a keyboard in order to enable the input of the ECV(t), ICV(t) and X(t) values In a particularly convenient embodiment the means for determining the ECV(t), and ICV(t) values and/or the means for determining the X(t) value are directly linked to the input unit which contains a corresponding interface in this case. The manual input of these values is then no longer necessary.

The invention also comprises a method for deriving a muscle weight $W_{muscle}(t)$ and/or a lean body mass LBM(t) of the patient at the time t. According to the invention the muscle weight $W_{muscle}(t)$ is derived by determining at least one anthropometric measure X(t) of the patient at the time t, determining the intracellular water volume ICV(t) of the patent at the time t, deriving the intracellular water volume $ICV_{basic}(t)$ of a first compartment with weight $W_{basic}(t)$ of the patient at the time t by using X(t), and deriving the muscle weight $W_{muscle}(t)$ as the weight of a second compartment of the patient by using $ICV_{basic}(t)$ and ICV(t).

As was outlined above muscle compartment is among those which exhibit a larger degree of individual variation. Due to the concept of the invention and unlike for the third compartment with weight $W_{hydr}(t)$, the weight of the muscle mass may be characterized without any measurement of the extracellular water of the patient. With the help of the determination of the basic weight $W_{basic}(t)$ it is—similar to the derivation of $ECV_{hydr}(t)$—possible to properly identify the weight of the muscle compartment of the patient.

The knowledge of $W_{muscle}(t)$ itself might be interesting for body composition analysis. In addition this provides for a possibility to calculate a lean body mass of the patient which is the dry weight of the patient excluding fat mass.

The invention also encompasses a device for deriving the muscle weight $W_{muscle}(t)$. This device is similar to the one described above except that there are no units necessary to enable entering and storing the ECV(t) value and that the microprocessor program storage unit comprises a program for deriving the muscle weight $W_{muscle}(t)$ of the second compartment by deriving the intracellular water volume $ICV_{basic}(t)$ of the first compartment of the patient at the time t by using the value(s) of X(t) and by deriving the weight $W_{muscle}(t)$ of the second compartment of the patient at the time t by using $ICV_{basic}(t)$ and ICV(t).

A computer storage medium on which a computer program is stored which is to be used in a device according to the invention for carrying out the methods according to the invention, is also constituting a part of the invention.

Various further embodiments of the invention are subject of the subclaims of the independent claims.

BRIEF DESCRIPTION OF THE DRAWING

For an improved understanding of the invention non-restrictive examples will be described with reference to the appended drawings in which.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustation only, since various changes and modifications within the spirit and scope of the invention will become apparent to those skilled in the art from this detailed description.

Figure 1:
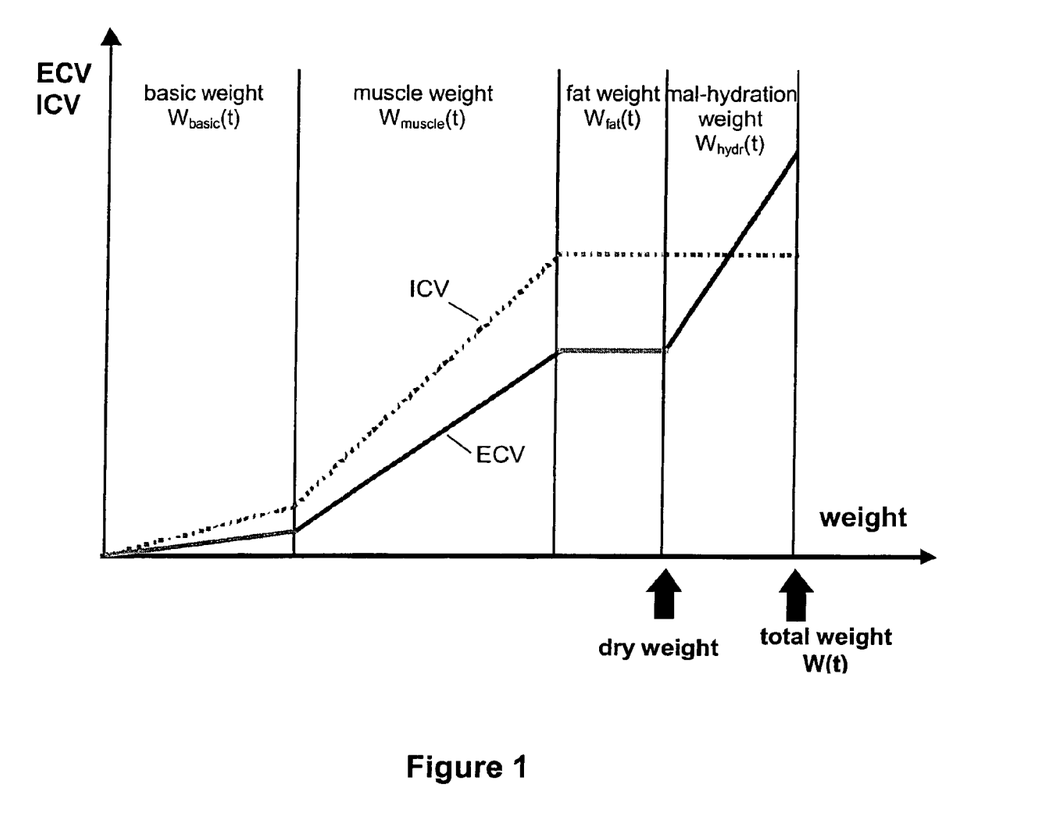
FIG. 1 shows a schematic illustration of the weight of a patient and four body compartments together with their ECV and ICV contributions, FIG. 2 schematically shows an embodiment of a device for determining the dry weight of a patient according to the invention.

As shown in FIG. 1 the total body weight W(t) may be regarded as the sum of the weights of four compartments:

$$W(t) = W_{basic}(t) + W_{muscle}(t) + W_{hydr}(t) + W_{fat}(t) \quad (2),$$

wherein the second compartment ($W_{sec}(t)$) has been assigned to the compartment $W_{muscle}(t)$ of muscle tissue which shall comprise the skeleton muscles, the third compartment $W_{hydr}(t)$ to the volume of mal-hydration fluid and the fourth compartment $W_{fat}(t)$ to the fat tissue.

The invention makes use of the observation that the weight $W_{basic}(t)$ of the first compartment, i.e. the basic weight, which shall consist of everything else than the named other tissues, i.e. muscles, fat and the mal-hydration fluid, remains largely constant from one individual to another as long as certain anthropometric measures $X(t)$ (detailed below) remain the same. The tissues which contribute to this first compartment comprise mainly bones, organs, blood and skin.

Different to the basic weight $W_{basic}(t)$ the weights of the second and fourth compartments, i.e. the muscle and the fat compartment with a muscle weight $W_{muscle}(t)$ and a fat weight $W_{fat}(t)$, exhibit by far the greatest degree of variability between different subjects. In the case of dialysis or other mal-hydrated patients, a third compartment must be included in order to take into account the hydration status or mal-hydration weight $W_{hydr}(t)$. For non-malhydrated, i.e. normohydrated patients the latter should be negligible or at least small, reflecting normal daily variations due to fluid intake and excretions.

The invention is further based on the observation that the ECV and ICV spaces contribute differently to these four compartments. The status of mal-hydration, in particular of overhydration, is particularly leading to a volume change in the ECV space while the ICV space remains mainly constant. Also the proportion of water contained in fat tissue may be assumed to be negligible.

As displayed in FIG. 1, in homeostasis a given basic and muscle weight is accompanied by specific values of ECV and ICV. To a good approximation ECV and ICV are linearly proportional to weight in these compartments (minor deviations are discussed below).

Figure 2:
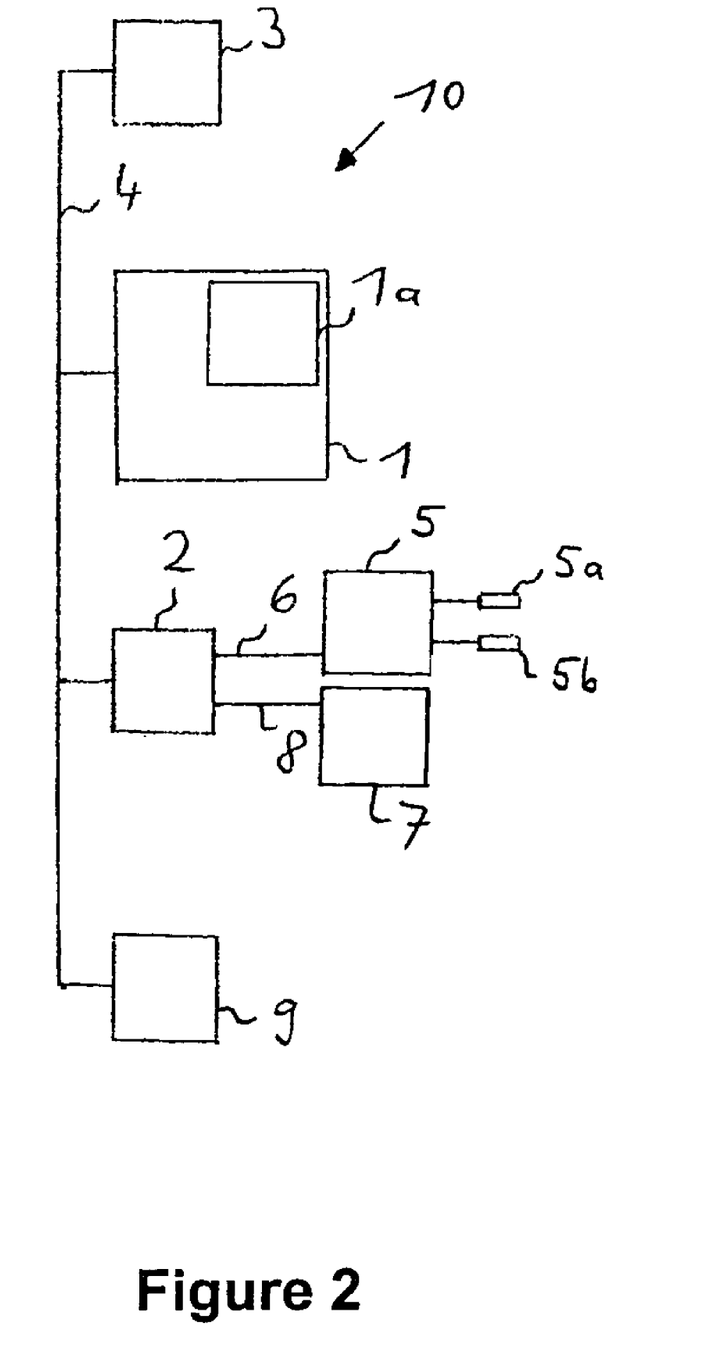

An example of the method according to the invention to determine the hydration status of a patient is now described with the help of an embodiment of a device according to the invention. Such an embodiment of a device for determining the ECV volume of a body compartment $W_{hydr}(t)$ of a patient is shown in FIG. 2. The device 10 comprises a microprocessor, unit 1 which in turn comprises a microprocessor program storage unit 1a. By means of a link 4, the microprocessor unit 1 is connected to an input unit 2 and a computer storage unit 3. A program for deriving the volume $ECV_{hydr}(t)$ of a patient at a time t is stored in the microprocessor program storage unit 1a.

The microprocessor program derives the volume $ECV_{hydr}(t)$, as follows: The extracellular and intracellular water volumes $ECV(t)$ and $ICV(t)$ of the subject at the time t are determined and entered into the input unit 2 which passes the values to the computer storage, unit 3 where they are stored.

Figure 3A:
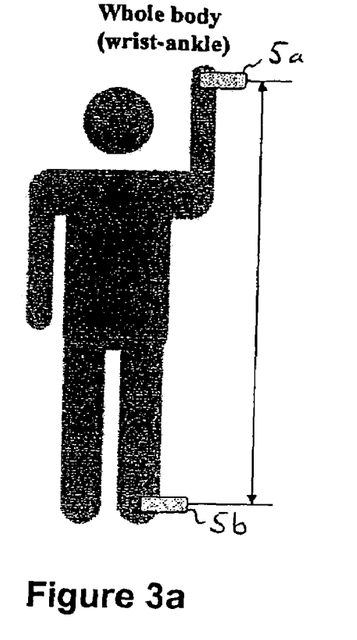
FIG. 3a shows a bioimpedance electrode arrangement for whole body bioimpedance measurements.
Figure 3B:
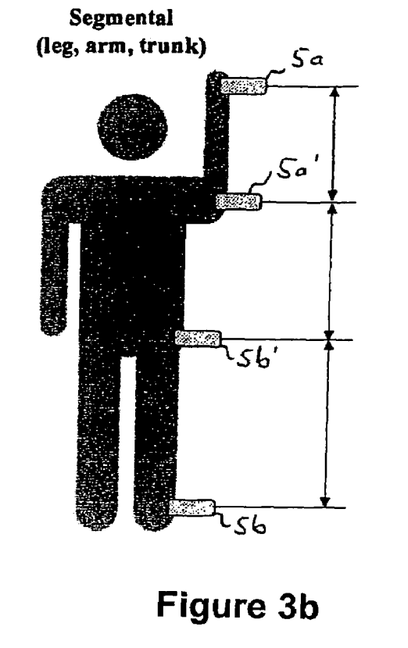
FIG. 3b shows a bioimpedance electrode arrangement for segmental body bioimpedance measurements.

To determine the $ECV(t)$ and $ICV(t)$ values, means 5 are provided which are connected to the input unit 2 by a link 6. The means 5 is a bioimpedance measurement device. For the bioimpedance measurement various electrode arrangements are possible. In FIG. 2 only two electrode elements 5a and 5b are attached to the bioimpedance measurement device 5. Each of the electrode units 5a and 5b consists of a current injection electrode and a potential pick up electrode (not shown). By applying the two electrode units 5a and 5b to thee wrist and the ankle of a patient, respectively, as outlined in FIG. 3a, the wholy body impedance may be determined. Under this electrode configuration the body may be regarded as a combination of several homogenous cylinders, representing trunk, legs and arms. By using additional electrodes on shoulder and hip, these cylindrical segments may be measured separately, thereby possibly increasing the accuracy of volume determinations. Such a configuration is displayed in FIG. 3b. Additional electrode units 5a' and 5b' are attached close to the corresponding shoulder and the hip of the patient enabling a segmental approach to the body elements leg, arm and trunk.

Figure 4:
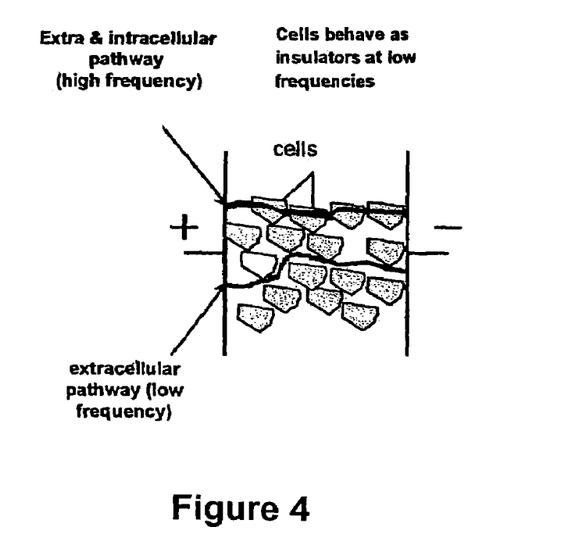
FIG. 4 shows an illustration of a bioimpedance measurement for determining the ECV and/or ICV contributions.

The ECV(t) value is determined by exploiting the fact that the electrical impedance of body tissue changes as alternating currents of different frequencies are applied to the patient via the electrodes. At low frequencies the cell membranes behave as insulators and the applied current passes only through the ECV spaces. At high frequencies the cell membranes become more conductive and thus current passes through both the ICV and ECV spaces. This is illustrated in FIG. 4. Measurement of the impedance over at least two frequencies, better over a range of frequencies, allows an impedance locus to be constructed from which the resistance of the ICV and ECV components may be determined. Hence the volumes of the respective compartments can then be calculated from the resistance information, based on compartment resistivity constants available from prior studies for which the volumes were also determined by dilution measurements.

A bioimpedance device performing such calculations is distributed by Xitron Technologies under the trademark HYDRA. Details about this device are disclosed in the international patent application WO 92/19153.

Returning to the embodiment shown in FIG. 2, means 7 are also provided for determining the height H(t) of the patient as an anthropometric measure X(t), which are connected to the input unit 2 by a link 8. The means 7 consist of a metering device which is well known in the art. In this advanced embodiment of the invention means 7 also comprises scales means for the determination of the weight W(t) of the patient.

In the embodiment shown in FIG. 2 the input unit 2 contains an interface by which the values for ECV(t), ICV(t), H(t) and W(t) are directly transferred via the link 4 to the computer storage unit 3. It may also be possible that the determined values for all or a part of the ECV(t), ICV(t), H(t) and W(t) values are manually entered into the input unit 2 by a user.

The program stored in the microprocessor storage unit 1a is now—with the help of stored previously established data—determining ECV and ICV contributions to some of the four compartments as is required to obtain the mal-hydration volume $ECV_{hydr}(t)$.

In a first step, the contributions $ECV_{basic}(t)$ and $ICV_{basic}(t)$ to the basic weight $W_{basic}(t)$ are derived. In order to determine the basic weight, all components of the body which are not muscle, fat or mal-hydration have to be identified. The main components or subcompartments of $W_{basic}(t)$ are bones, organs, blood and skin. One therefore has $$W_{basic}(t) = \sum_i W_{basic,i}(t), \quad (3)$$

here $W_{basic}(t) =$ (3.1)
$W_{basic,bones}(t) + W_{basic,organs}(t) + W_{basic,blood}(t) + W_{basic,skin}(t).$ It is a useful approximation to assume that there are mass fraction percentages for these subcompartments which refer to an average weight $W_{av}$ in a population in dependence on at least one anthropometric measure $X(t)$. The height $H(t)$ of the patient has turned out to be a very valuable parameter to be used for such a purpose. The average weight $W_{av}$ is the weight to be expected if muscle and fat content (as well as mal-hydration) are comparable to the population mean used.

Figure 5:
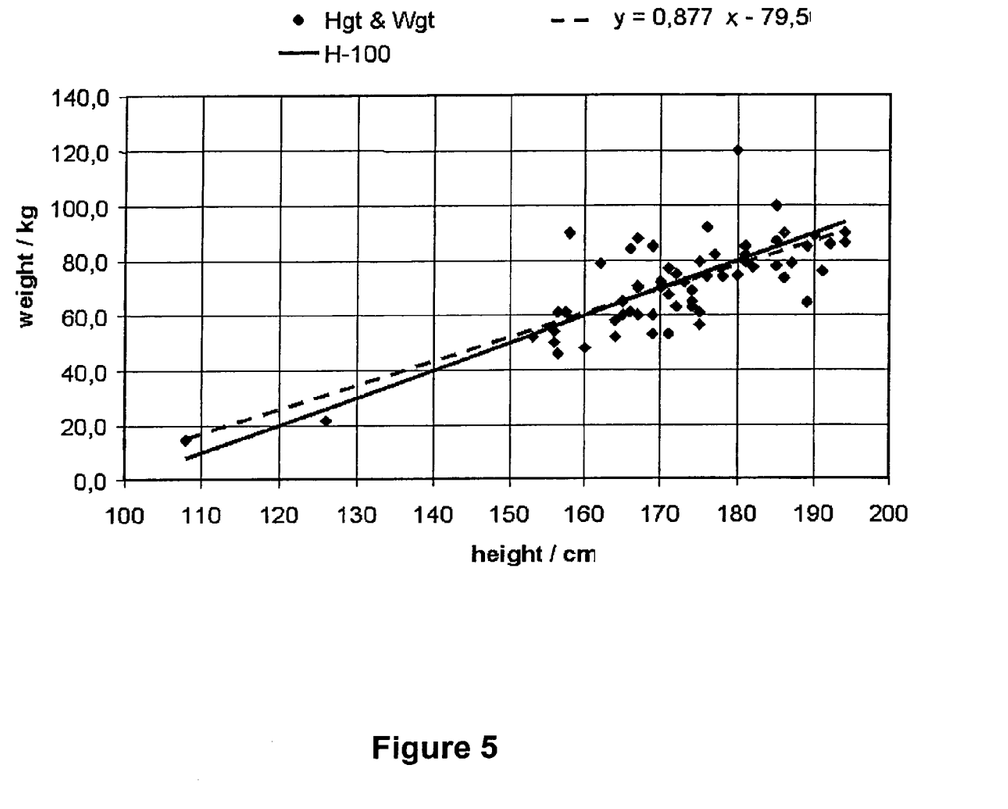
FIG. 5 shows the dependence of an average weight of a population on the height of an individual.

In FIG. 5 weight is plotted versus height ("Hgt & Wgt") for a mixed male/female reference population (without kidney disease). Despite height clearly is a dominant factor influencing weight, there is a considerable weight variation for a given height, which is explained by fat and muscle mass variations between persons of same height.

In FIG. 5 possible relationships between $H(t)$ and $W_{av}(t)$ are also illustrated. The dashed line shows a regression analysis result with $$W_{av}(H(t))=k_{HW}(H(t)-H_0) \quad (4),$$

where $k_{HW}$=0,877 kg/cm and $H_0$=90,7 cm. A useful approximation for a height range from 150 cm to 200 cm is $k_{HW}$=1 kg/cm and $H_0$=100 cm ("H-100" line in FIG. 5).

In FIG. 5 males and females were not distinguished since for both the same relation was observed. Nevertheless improved relationships replacing equation (4), involving various further data like sex, age etc. might be constructed without departing from the general concept of this invention.

The mass fractions of the subcompartments on this average weight $W_{av}(t)$ are—at least partly—taken from previously established data (H. Skelton: The storage of water by various tissues of the body, Arch. Int. Med. 40, 140 (1972); H. C. Lukaski, Estimation of muscle mass, chap. 6, in Human Body Composition, edited by A. F. Roche, S. B. Heymsfield and T. G. Lohman, Human Kinetics, 1996, p. 109–128; H. Rico, M. Revilla and E. R. Hernadez: Sex differences in the acquisition of total bone mineral mass peak assessed through dual-energy x-ray absorbitometry, Calcified Tissue International 51, 251 (1992); E. Witzleb: Funktionen des Gefäβsystems, chap. 20, in: Physiologie des Menschen, edited by R. F. Schmidt and G. Thews, Berlin-Heidelberg, Springer-Verlag, 1987, p. 505–571; C. Weiss and W. Jelkmann, Funktionen des Blutes, chap. 18, in: Physiologie des Menschen, edited by R. F. Schmidt and G. Thews, Berlin-Heidelberg, Springer-Verlag, 1987, p. 422–460; D. DuBois and E. F. DuBois: A formula to estimate the approximate surface area if height and weight be known, Arch Int Med 17, 863 (1916)). Hence for the subcompartment weights $W_{basic,i}(t)$ the following relation is used:

$$W_{basic,i}(t)=k_i W_{av}(H(t)) \quad (5).$$

Figure 6:
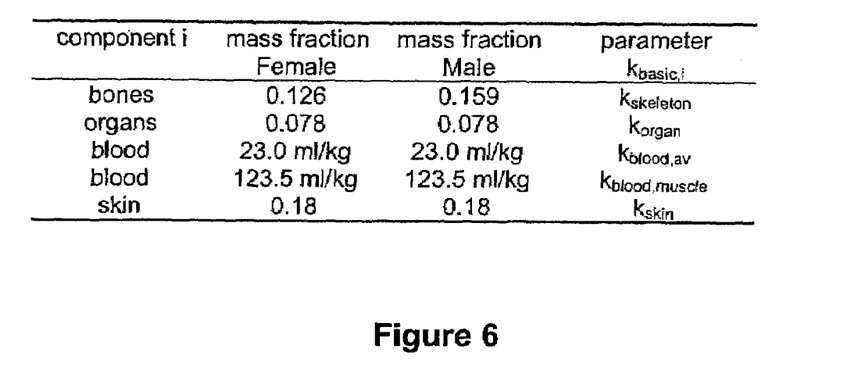
FIG. 6 shows a compilation of numerical values for the coefficients $k_i$ relating the basic weights $W_{basic,i}$ to the average weight $W_{av}$.

The fractions $k_i$ as extracted from the literature are summarized in a table in FIG. 6. It is important to mention that fractions $k_{HW}$ (relating average weight to height) and $k_i$ (relating basic weight components to average weight) are dependent on the population selected for deriving these parameters, though the $W_{basic,i}$ are expected to exhibit only a minor dependence due to the concept how the basic weight $W_{basic}$ is defined. Due to this concept first reliable results for the hydration status are already obtained with the data of FIGS. 5 and 6 which were derived from various literature sources for which the reference populations are likely to have differed. Nonetheless the precision of the $W_{basic,i}$ should be particularly accurate if $k_{HW}$ and $k_i$ have been determined for the same population.

For the bones it has turned out to be useful to distinguish between males and females. This is caused by the fact that mineral bone content is different between males and females. For the other subcompartments such a differentiation has not been found necessary in order to yield reasonable results.

For $W_{basic,blood}(t)$ it has proved helpful to apply a further refinement. Though blood is contained in organs and in the arterial and venous vessels supplying organs and muscles, it is also considerably distributed in the muscle tissue. Once one has attributed the mass variability from one individual to another to the muscle and the fat compartment, the volume of the blood mass compartment is consequently decomposed into one part which is only dependent on the anthropometric parameter as in equation (5) and into a second part which depends on the mass of the muscle department:

$$V_{basic,blood}(t)=k_{blood,av}W_{av}(H(t))+k_{blood,muscle}W_{muscle}(t) \quad (6),$$

where $k_{blood,av}$ and $k_{blood,muscle}$ are empirical coefficients which are also given in FIG. 6.

Blood mass varies slightly due to the haematocrit $Hct(t)$. If the density of plasma is assumed to be constant, then the mass of blood may be expressed as $$W_{basic,blood}(t)=V_{basic,blood}(t)((1-Hct(t))\rho_{pl}+Hct(t)\rho_{ery}) \quad (7),$$

where $\rho_{pl}$ is the blood plasma density (1,027 kg/litre) and $\rho_{ery}$ is the erythrocyte density (1,096 kg/litre). In a first approximation the method according to the invention may be applied by assuming a fixed average value for $Hct(t)$ since the deviations due to variations of the haematocrit are small. Should the haematocrit however have been determined, the application of equation (7) is a useful improvement.

The skin occupies a relatively large mass fraction (ca. 18%) which includes the subcutaneous tissue. Some fat is likely to be contained in this subcutaneous component. However, this "basic fat" together with any other tissue may be regarded collectively as "the skin", and is not included in the fat component to be calculated below.

The skin mass is regarded to be independent of sex, but dependent on body surface area (BSA). If a person gains much weight at same height, it is expected that skin is not just stretched, but additional skin accumulates. After weight loss the opposite should happen. Therefore skin mass should not only be scaled according to the average weight. Additionally a factor relating real BSA to BSA at average weight for the given height should be considered:

$$W_{basic,skin}(t) = k_{skin} W_{av}(t) \frac{BSA(W(t), H(t))}{BSA(W_{av}(t), H(t))}. \quad (8)$$

For the calculation of the body surface area BSA(W,H) an expression given by DuBois and DuBois (D. DuBois and E. F. DuBois: A formula to estimate the approximate surface area if height and weight be known, Arch Int Med 1916 17, 863 (1916)) may be used:

$$BSA(W, H)[cm^2]=71,84(W[kg])^{0,425}(H[cm])^{0,725} \quad (9).$$

Regarding equations (3) to (9) is hence possible—taking the determined values of the anthropometric parameter $H(t)$ and the weight $W(t)$—to determine the basic weight $W_{basic}(t)$. The total weight $W(t)$ is actually only entering the calculation as a kind of second order effect for the derivation of $W_{basic,skin}(t)$ according to equation (8). If in a first approximation $W_{basic,skin}(t)$ is taken to be dependent on $W_{av}(t)$ only, the total weight $W(t)$ would not be required for the calculation of $W_{basic}(t)$.

According to equation (6) it is however necessary to also determine $W_{muscle}(t)$ in order to derive $W_{basic,blood}(t)$ and thus $W_{basic}(t)$. This point will be addressed further below.

The method of the invention which is implemented in the program stored in the microprocessor storage unit 1a is now taking advantage of the determined ECV(t) and ICV(t) values and compares them with some of the ECV and ICV contributions of the various compartments. For the first compartment $W_{basic}$ one has:

$$ECV_{basic}(t) = \sum_i ECV_{basic,i}(t), \quad (10.1)$$

$$ICV_{basic}(t) = \sum_i ICV_{basic,i}(t). \quad (10.2)$$

Each subcompartment $W_{basic,i}(t)$ will contribute differently to the ECV and ICV spaces. It has been proved reasonable to take the $ECV_{basic,i}(t)$ and $ICV_{basic,i}(t)$ contributions to be linearly proportional to $W_{basic,i}(t)$:

$$ECV_{basic,i}(t) = \lambda_{ECV,i} W_{basic,i}(t) \quad (11.1),$$

$$ICV_{basic,i}(t) = \lambda_{ICV,i} W_{basic,i}(t) \quad (11.2).$$

Figure 7:
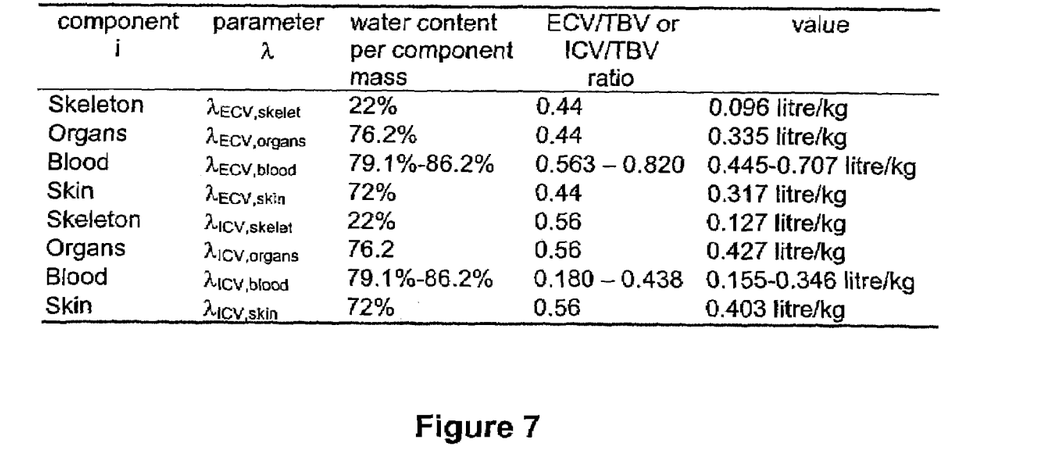
FIG. 7 shows a compilation of numerical values for the coefficients $\lambda_{ECV}$ and $\lambda_{ICV}$ relating the basic weight subcompartments to their ECV and ICV contributions and FIG. 8 shows a graphical overview of the method according to the invention to derive various body compartment masses.

Examples of values of the coefficients $\lambda_{ECV,i}$ and $\lambda_{ICV,i}$ which have been extracted from the literature are compiled in FIG. 7. For $\lambda_{ECV,blood}$ and $\lambda_{ICV,blood}$ similar corrections like equation (7) may be used which take into account any dependence on the haematocrit. Such corrections start from the concept that $ECV_{basic,blood}(t)$ is made up by the blood plasma volume and $ICV_{basic,blood}(t)$ is made up by the blood cell volume. The shown values for $\lambda_{ECV,blood}$ and $\lambda_{ICV,blood}$ were accordingly calculated for a range of the haematocrit from 22% to 50%, this range covering the range of normohydrated patients and the low haematocrit range of dialysis patients.

With the help of equations (10.1) to (11.2) it is now possible to deduce the extracellular water volume $ECV_{basic}(t)$ of the first (basic) compartment and to do the same for the intracellular water volume $ICV_{basic}(t)$.

Referring to FIG. 1 the following relationship is found, taking into account that the mal-hydration weight $W_{hydr}(t)$ and the fat weight $W_{fat}(t)$, i.e. the third and fourth compartments, have only negligible ICV contents:

$$ICV_{muscle}(t) = ICV(t) - ICV_{basic}(t) \quad (12).$$

Since the second compartment, i.e. the muscle tissue, has a specific ratio of extra- to intracellular water volumes, $$\gamma = \frac{ECV_{muscle}(t)}{ICV_{muscle}(t)}, \quad (13)$$

(from population data $\gamma = 0.582$ has been derived) it is possible to derive the volume of $ECV_{muscle}(t)$ as $$ECV_{muscle}(t) = (ICV(t) - ICV_{basic}(t))\gamma \quad (14).$$

Considering further a fixed fraction $\lambda_{TBW\_muscle}$ of water per unit mass of muscle, the muscle weight $W_{muscle}(t)$ is derived as $$W_{muscle}(t) = \frac{ECV_{muscle}(t) + ICV_{muscle}(t)}{\lambda_{TBW\_muscle}} = \frac{(ICV(t) - ICV_{basic}(t))(1+\gamma)}{\lambda_{TBW\_muscle}}, \quad (15)$$

where $\lambda_{TBW\_muscle} = 0{,}757$ litres/kg is taken from the literature.

With equation (15) $W_{muscle}(t)$ is now calculated, a parameter which already was required for equation (6), introducing a small improvement for blood volume calculation. By means of an appropriate computer program a method might be applied which solves the equations by an iterative procedure which is well known in the art, e.g. starting with a population average value for $W_{muscle}(t)$ and iteratively repeating calculations in equations (6) to (15) until consistent data are found.

It is worth noting that the small dependence between $W_{basic}(t)$ and $W_{muscle}(t)$ might also be entangled by using a slightly different definition for $W_{basic,blood}(t)$: Instead of assigning the blood contained in the muscle compartment to the blood subcompartment of the basic compartment, it is also possible to assign it to the muscle compartment. The second term in equation (6) is then added to $W_{muscle}(t)$ instead of leading to a contribution to $W_{basic,blood}(t)$. The parameters for both compartments may then be derived directly. This alternative approach only represents an equivalent mathematical approach which is not departing from the concept of the invention.

The program stored in the microprocessor storage unit 1a is now able to derive the $ECV_{hydr}(t)$ component of the third compartment $W_{hydr}(t)$ by again taking into account the situation shown in FIG. 1: Assuming first that all mal-hydration is sequestered in the, ECV space and second that the fourth compartment, the fat compartment, does not contribute to the measured ECV(t), this $ECV_{hydr}(t)$ component is derived by equation (1).

Another parameter frequently used to characterize nutrition status is the lean body mass, (LBM), On the basis of the concept described, this parameter LBM(t) is simply the sum of basic and muscle, compartments, i.e.

$$LBM(t) = W_{basic}(t) + W_{muscle}(t) \quad (16).$$

The value for LBM(t) may thus easily also be derived. Especially for mal-hydrated patients the concept of this invention should allow a more precise determination of LBM, since other known concepts to determine LBM usually cannot distinguish between tissue and excess fluid, i.e. there is the danger that a malnourished and overhydrated patient might be erroneously characterized as being well-nourished and normohydrated.

Once $ECV_{hydr}(t)$ has been determined, in a further mode of the invention the corresponding weight $W_{hydr}(t)$ is also derived by the microprocessor program by simply multiplying $ECV_{hydr}(t)$ by $\rho_{ECV}(=1$ kg/litre). The weight $W_{fat}(t)$ of the fourth compartment may then additionally be derived from equation (2) by solving for this variable. The dry weight—if required—may be derived by subtracting $W_{hydr}(t)$ from W(t).

Figure 8:
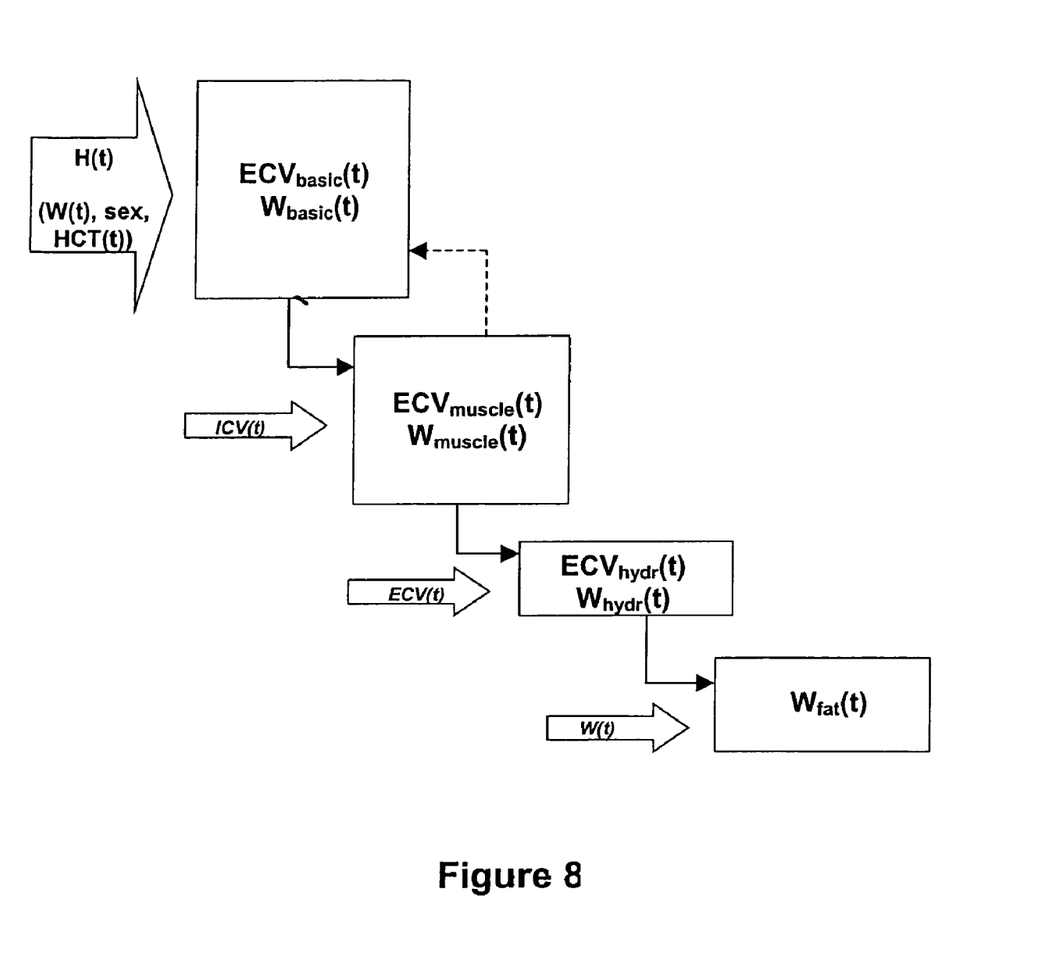

The whole procedure by which the program progresses in order to derive the various results is summarized by FIG. 8.

The result for $ECV_{hydr}(t)$ or $W_{hydr}(t)$ is finally passed on to an output unit 9 which is a display device and which displays the result to a user. Further results—independent whether intermediate or as further result like the weight $W_{fat}(t)$—might add to the informative character of the display.

The compartmental results may be stored in the device to enable a trend analysis including previously derived results. It has also proved useful to smooth the data by deriving weighted average values from the latest and the previous data. For this purpose various algorithms are available in the art to reduce statistical scatter in the data. A useful improvement in the averaging procedure for the current result to be displayed was obtained by giving the latest measurement the highest weight and by decreasing the weight of other, previous measurements with increasing time that has passed since the measurements were taken.

The disclosed device and method according to the invention is hence able to provide for a powerful technique for the management of dry weight. In case the weight $W_{fat}(t)$ of the fat mass compartment and/or the weight $W_{muscle}(t)$ of the muscle mass compartment are also determined the invention is yielding useful further results which allow conclusions about the nutritional status of the patient This is of course not dependent on whether the patient is really mal-hydrated or not Hence management of any individual is possible, independent of any treatment modality. The invention is particularly applicable for patients which undergo end stage renal failure treatments like hemodialysis, hemofiltration, hemodiafiltration or any forms of peritoneal dialysis (all these treatment modalities are summarized throughout this patent application by the terminology "a dialysis treatment"). A characterization of hydration status might also be highly desirable within the intensive care setting, since highly abnormal electrolyte- and fluid conditions are frequent for such patients. Furthermore, measurement in virtually any setting where nutrition or fitness parameters are required, including home, pharmacies, medical practices, dialysis units, wards, fitness centers, etc, would be practical.

The invention being thus described, it will be apparent that the same may be varied in many ways. Such variations are not to be regarded as a departure from the spirit and scope of the invention, and all such modifications as would be recognized by one skilled in the art are intended to be included whithin the scope of the following claims.

The invention claime is:

1. A method for determining the volume of a body compartment $ECV_{hydr}hydr(t)$ of a patient at a time t in order to manage a hydration level of said patient comprising the steps of:
   determining at least one anthropometric measure $X(t)$ of the patient at the time t;
   determining the extracellular water volume $ECV(t)$ of the patient at the time;
   determining the intracellular water volume $ICV(t)$ of the patient at the time t;
   deriving the extracellular water volume $ECV_{basic}(t)$ of a first compartment with weight $W_{basic}(t)$ of the patient at the time t by using $X(t)$;
   deriving the extracellular water volume $ECV_{sec}(t)$ of a second compartment with weight $W_{sec}(t)$ of the patient at the time t by using $ICV(t)$;
   deriving the volume $ECV_{hydr}hydr(t)$ as the extracellular water volume of a third compartment of the patient with weight $W_{hydr}(t)$ by using the equation $ECV_{hydr}(t)=ECV(t)-ECV_{basic}(t)-ECV_{sec}(t)$; and managing the hydration level of said patient using said derived volume $ECV_{hydr}(t)$.

2. The method according to claim 1 wherein the second compartment represents the muscle tissue with weight $W_{muscle}(t)$ and the extracellular water volume $ECV_{muscle}(t)$.

3. The method according to claim 1 wherein the intracellular water volume $ICV_{basic}(t)$ of the first compartment is also derived from $X(t)$ and that $ICV_{basic}(t)$ is also used to derive $ECV_{sec}(t)$.

4. The method according to claim 1 wherein the weight $W(t)$ of the patient at time t is determined and that the extracellular water volume $ECV_{basic}(t)$ and/or the intracellular water volume $ICV_{basic}(t)$ of the first compartment are derived by using $X(t)$ and $W(t)$.

5. The method according to claim 1 wherein at the extracellular and/or intracellular water volumes $ECV_{basic}(t)$ and $ICV_{basic}(t)$ of the first compartment are derived by also using $ICV(t)$.

6. The method according to claim 1 wherein the at least one anthropometric measure $X(t)$ is the height $H(t)$ of the patient at the time t.

7. The method according to claim 1 wherein $ECV(t)$ and $ICV(t)$ are derived from a bioimpedance measurement.

8. The method according to claim 1 wherein $ECV_{basic}(t)$ is derived from various subcompartments by the following equation:

$$ECV_{basic}(t) = \sum_i ECV_{basic,i}(t),$$

where $ECV_{basic,i}(t)$ is the ECV of the $i^{th}$ subcompartment of the first compartment at the time t.

9. The method according to claim 1 wherein at least one of the i $ECV_{basic,i}(t)$ values is derived as proportional part of the weight $W_{basic,i}(t)$ of the $i^{th}$ subcompartment, i.e.

$ECV_{basic,i}(t)=\lambda_{ECV,i}W_{basic,i}(t),$ where $\lambda_{ECV,i}$ is the corresponding proportionality constant.

10. The method according to claim 1 wherein $ICV_{basic}(t)$ is derived from various subcompartments by the following equation:

$$ICV_{basic}(t) = \sum_i ICV_{basic,i}(t),$$

where $ICV_{basic,i}(t)$ is the ICV of the $i^{th}$ subcompartment of the first compartment at the time t.

11. The method according to claim 10 wherein at least one of the i $ICV_{basic,i}(t)$ values is derived as proportional part of the weight $W_{basic,i}(t)$ of the $i^{th}$ subcompartment, i.e.

$ICV_{basic,i}(t)=\lambda_{ICV,i}W_{basic,i}(t),$ where $\lambda_{ICV,i}$ is the corresponding proportionality constant.

12. The method according to claim 8 wherein the subcompartments comprise four subcompartments representing the skeleton ($ECV_{basic,sceleton}$, $ICV_{basic,sceleton}$, $W_{basic,skeleton}$), organs ($ECV_{basic,organ}$, $ICV_{basic,organ}$, $W_{basic,organ}$), blood ($ECV_{basic,blood}$, $ICV_{basic,blood}$, $W_{basic,blood}$) and skin ($ECV_{basic,skin}$, $ICV_{basic,skin}$, $W_{basic,skin}$).

13. The method according to claim 6 wherein an average weight $W_{av}(H(t))$ is derived from the measured height $H(t)$ of a patient and a previously established H against $W_{av}(H)$ relation for a reference population and that at least one of the subcompartmental weights $W_{basc,i}$ is derived by $W_{basic,i}(t)=k_i W_{av}(H(t)),$ where $k_i$ is the corresponding proportionality constant.

14. The method according to claim 12 wherein the relation for $W_{basic,i}(t)$ is used for the skeleton and the organ subcompartment.

15. The method according to claim 12 wherein the haematocrit $Hct(t)$ of the patient at the time t is determined and that $Hct(t)$ is used to claim derive $W_{basic,blood}(t)$.

16. The method according to claim 12 wherein the body surface area index (BSA(t)) of the patient at the time t is determined and that BSA(t) is used to derive $W_{basic,skin}(t)$.

17. The method according to claim 4 wherein the masses $W_{basic}(t)$, $W_{sec}(t)$ and $W_{hydr}(t)$ of the first, second and third compartments are derived and that the mass $W_{fat}(t)$ of a fourth compartment of the patient at the time t is derived by the following formulae:

$$W_{fat}(t)=W(t)-W_{basic}(t)-W_{sec}(t)-W_{hydr}(t).$$

18. A method for determining a muscle weight $W_{muscle}(t)$ of a patient at a time t comprising the steps of:
   determining at least one anthropometric measure X(t) of the patient at the time t; determining the intracellular water volume ICV(t) of the patient at the time t;
   deriving the intracellular water volume $ICV_{basic}(t)$ of a first compartment with weight $W_{basic}(t)$ of the patient at the time t by using X(t);
   deriving the muscle weight $W_{muscle}(t)$ as the weight of a second compartment of the patient by using $ICV_{basic}(t)$ and ICV(t); and
   assessing a nutrition and fitness status of said patient using the derived muscle weight $W_{muscle}(t)$ and using said status to manage care of said patient.

19. The method according to claim 18 wherein $W_{muscle}(t)$ is derived by the relation $$W_{muscle}(t) = \frac{(ICV(t) - ICV_{basic}(t))(1+\gamma)}{\lambda_{TBW\_muscle}},$$

where γ is the ratio between the extracellular water to intracellular water volume in the second compartment and $\lambda_{TBW\_muscle}$ is the fraction of water per unit mass in the second compartment.

20. The method according to claim 18 wherein the weight $W_{basic}(t)$ of the first compartment of the patient at the time t is also derived by using X(t).

21. The method according to claim 20 wherein a lean body mass LBM(t) of the patient at the time t is derived by using the equation $$LBM(t)=W_{basic}(t)+W_{muscle}(t).$$

22. The method according to claim 18 wherein the first compartment comprises the skeleton, organs, blood and skin of the patient.

23. A device for determining the volume of a body compartment $ECV_{hydr}(t)$ of a patient at a time t by determining at least one anthropometric measure X(t) of the patient at the time t, determining the extracellular water volume ECV(t) of the patient at the time t, determininq the intracellular water volume ICV(t) of the patient at the time t, deriving the extracellular water volume $ECV_{basic}(t)$ of a first compartment with weight $W_{basic}(t)$ of the patient at the time t by using X(t), deriving the extracellular water volume $ECV_{sec}(t)$ of a second compartment with weight $W_{sec}(t)$ of the patient at the time t by using ICV(t), and deriving the volume $ECV_{hydr}(t)$ as the extracellular water volume of a third compartment of the patient with weight $W_{hydr}(t)$ by using the equation, $ECV_{hydr}(t)=ECV_{basic}(t)-ECV_{sec}(t)$, the device comprising:

a microprocessor unit which includes a microprocessor program storage unit;
an input unit to claim enable entering values of ECV(t), ICV(t) and X(t);
a computer storage unit for storing the ECV(t), ICV(t) and X(t) values; and
said microprocessor program storage unit including a program for deriving the extracellular water volume $ECV_{hydr}(t)$ by deriving the extracellular water volume $ECV_{basic}(t)$ of the first compartment with weight $W_{basic}(t)$ of the patient at the time t by using the value(s) of X(t), by deriving the extracellular water volume $ECV_{sec}(t)$ of the second compartment with weight $W_{sec}(t)$ of the patient at the time t by using the value of ICV(t), and by deriving the volume $ECV_{hydr}(t)$ as the extracellular water volume of the third compartment of the patient with weight $W_{hydr}(t)$ by using the equation $$ECV_{hydr}(t)=ECV(t)-ECV_{basic}(t)-ECV_{sec}(t).$$

24. The device according to claim 23 wherein said device further comprises means for determining the ECV(t) and ICV(t) values.

25. The device according to claim 23 wherein said device further comprises means for determining the values of the at least one anthropometric measure X(t) and/or the weight W(t) of the patient at the time t.

26. The device according to claim 24 wherein said means for determining the ECV(t) and ICV(t) values is a bioimpedance measurement device.

27. The device according to claim 23 wherein the input unit is a manual user interface.

28. The device according to claim 23 wherein the input unit includes an interface for means for determining the ECV(t) and ICV(t) values and/or means for determining the X(t) and/or W(t) values.

29. The device according to claim 23 further comprising an output unit that is linked to claim the microprocessor unit for outputting the derived $ECV_{hydr}(t)$ value.

30. The device according to claim 23 wherein the input unit is enabled to claim receive a value for the haematocrit Hct(t) of the blood of the patient at the time t and the computer storage unit is enabled to claim store said Hct(t) value and the program stored in the microprocessor program storage unit corrects the weight of the first compartment $W_{basic}(t)$ for the value of the haematocrit.

31. A device for determining a muscle weight $W_{muscle}(t)$ of a patient at a time t by determining at least one anthropometric measure X(t) of the patient at the time t, determining the intracellular water volume ICV(t) of the patient at the time t, deriving the intracellular water volume $ICV_{basic}(t)$ of a first compartment with weight $W_{basic}(t)$ of the patient at the time t by using X(t), and deriving the muscle weight $W_{muscle}(t)$ as the weight of a second compartment of the patient by using $ICV_{basic}(t)$ and ICV(t), the device comprising:

a microprocessor unit including a microprocessor program storage unit;
an input unit to claim enable entering values of ICV(t) and X(t);
a computer storage unit for storing the ICV(t) and X(t) values; and
said microprocessor program storage unit including a program for deriving the muscle weight $W_{muscle}(t)$ of the second compartment by deriving the intracellular water volume $ICV_{basic}(t)$ of the first compartment with weight $W_{basic}(t)$ of the patient at the time t by using the value(s) of X(t), and by deriving the weight $W_{muscle}(t)$ of the second compartment of the patient at the time t by using $ICV_{basic}(t)$ and ICV(t).

32. A microprocessor program storage medium having stored thereon a program for determining a muscle weight $W_{muscle}(t)$ of a patient at a time t using at least one anthropometric measure X(t) and the intracellular water volume ICV(t) of the patient at the time t, said program on said storage medium deriving the intracellular water volume $ICV_{basic}(t)$ of a first compartment with weight $W_{basic}(t)$ of the patient at the time t by using X(t), and deriving the muscle weight $W_{muscle}(t)$ as the weight of a second compartment of the patient by using $ICV_{basic}(t)$ and ICV(t).

33. A microprocessor program storage medium having stored thereon a program for determining the volume of a body compartment $ECV_{hydr}(t)$ of a patient at a time t using at least one anthropometric measure X(t), the extracellular water volume ECV(t) and the intracellular water volume ICV(t) of the patient at the time t, said program on said storage medium deriving the extracellular water volume $ECV_{basic}(t)$ of a first compartment with weight $W_{basic}(t)$ of the patient at the time t by using X(t), deriving the extracellular water volume $ECV_{sec}(t)$ of a second compartment with weight $W_{sec}(t)$ of the patient at the time t by using ICV(t), and deriving the volume $ECV_{hydr}(t)$ as the extracellular water volume of a third compartment of the patient with weight $W_{hydr}(t)$ by using the equation, $$ECV_{hydr}(t)=ECV(t)-ECV_{basic}(t)-ECV_{sec}(t).$$

34. A method for determining the volume of a body compartment $ECV_{hydr}(t)$ of a patient at a time t comprising the steps of:
    conducting a measurement of the patient at the time t to determine at least one anthropometric measure X(t) of the patient;
    conducting a measurement of the patient at the time (t) to determine the extracellular water volume ECV(t) of the patient;
    conducting a measurement of the patient at the time t to determine the intracellular water volume ICV(t) of the patient;
    deriving the extracellular water volume $ECV_{basic}(t)$ of a first compartment with weight $W_{basic}(t)$ of the patient at the time t by using X(t);
    deriving the extracellular water volume $ECV_{hydr}sec(t)$ of a second compartment with weight $W_{sec}(t)$ of the patient at the time t by using ICV(t); and
    deriving the volume $ECV_{hydr}(t)$, which is a measure of hydration status of the patient, as the extracellular water volume of a third compartment of the patient with weight $W_{hydr}(t)$ by using the equation $$ECV_{hydr}(t)=ECV(t)-ECV_{basic}(t)-ECV_{sec}(t).$$

35. The method according to claim 34 wherein the second compartment represents the muscle tissue with weight $W_{muscle}(t)$ and the extracellular water volume $ECV_{muscle}(t)$.

36. The method according to claim 34 wherein the intracellular water volume $ICV_{basic}(t)$ of the first compartment is also derived from X(t) and that $ICV_{basic}(t)$ is also used to claim derive $ECV_{sec}(t)$.

37. The method according to claim 34 wherein the weight W(t) of the patient at time t is determined and that the extracellular water volume $ECV_{basic}(t)$ and/or the intracellular water volume $ICV_{basic}(t)$ of the first compartment are derived by using X(t) and W(t).

38. The method according to claim 34 wherein at the extracellular and/or intracellular water volumes $ECV_{basic}(t)$ and $ICV_{basic}(t)$ of the first compartment are derived by also using ICV(t).

39. The method according to claim 34 wherein the at least one anthropometric measure X(t) is the height H(t) of the patient at the time t.

40. The method according to claim 34 wherein ECV(t) and ICV(t) are derived from a bioimpedance measurement.

41. The method according to claim 34 wherein $ECV_{(t)}$ is derived from various subcompartments by the following equation:

$$ECV_{basic}(t) = \sum_i ECV_{basic,i}(t),$$

where $ECV_{basic,i}(t)$ is the ECV of the $i^{th}$ subcompartment of the first compartment at the time t.

42. The method according to claim 34 wherein at least one of the i $ECV_{basic,i}(t)$ values is derived as proportional part of the weight $W_{basic,i}(t)$ of the ith subcompartment, i.e.

$$ECV_{basic,i}(t)=\lambda_{ECV,i}W_{basic,i}(t),$$

where $\lambda ECV,i$ is the corresponding proportionality constant.

43. The method according to claim 34 wherein $ICV_{basic}(t)$ is derived from various subcompartments by the following equation:

$$ICV_{basic}(t) = \sum_i ICV_{basic,i}(t),$$

where $ICV_{basic,i}(t)$ is the ICV of the $i^{th}$ subcompartment of the first compartment at the time t.

44. The method according to claim 43 wherein at least one of the i $ICV_{basic,i}(t)$ values is derived as proportional part of the weight $W_{basic,i}(t)$ of the $i^{th}$ subcompartment, i.e.

$$ECV_{basic,i}(t)=\lambda_{ICV,i}W_{basic,i}(t),$$

where $\lambda_{ICV,i}$ is the corresponding proportionality constant.

45. The method according to claim 41 wherein the subcompartments comprise four subcompartments representing the skeleton ($ECV_{basic,sceleton}$, $ICV_{basic,sceleton}$, $W_{basic,skeleton}$), organs ($ECV_{basic,organ}$, $ICV_{basic,organ}$, $W_{basic,organ}$), blood ($ECV_{basic,blood}$, $ICV_{basic,blood}$, $W_{basic,blood}$) and skin ($ECV_{basic,skin}$, $ICV_{basic,skin}$, $W_{basic,skin}$).

46. The method according to claim 39 wherein an average weight $W_{av}(H(t))$ is derived from the measured height H(t) of a patient and a previously established H against $W_{av}(H)$ relation for a reference population and that at least one of the subcompartmental weights $W_{basic,i}$ is derived by $$W_{basic,i}(t)=k_iW_{av}(H(t)),$$

where $k_i$ is the corresponding proportionality constant.

47. The method according to claim 44 wherein the relation for $W_{basic,i}(t)$ is used for the skeleton and the organ subcompartment.

48. The method according to claim 44 wherein the haematocrit Hct(t) of the patient at the time t is determined and that Hct(t) is used to claim derive $W_{basic,blood}(t)$.

49. The method according to claim 45 wherein the body surface area index (BSA(t)) of the patient at the time t is determined and that BSA(t) is used to claim derive $W_{basic,skin}(t)$.

50. The method according to claim 37 wherein the masses $W_{basic}(t)$, $W_{sec}(t)$ and $W_{hydr}(t)$ of the first, second and third compartments are derived and that the mass $W_{fat}(t)$ of a fourth compartment of the patient at the time t is derived by the following formulae:

$$W_{fat}(t) = W(t) - W_{basic}(t) - W_{sec}(t) - W_{hydr}(t).$$

51. A method for determining a muscle weight $W_{muscle}(t)$ of a patient at a time t comprising the steps of:
   conducting a measurement of the patient at the time t to determine at least one anthropometric measure $X(t)$ of the patient;
   conducting a measurement of the patient at the time t to determine the intracellular water volume $ICV(t)$ of the patient;
   deriving the intracellular water volume $ICV_{basic}(t)$ of a first compartment with weight $W_{basic}(t)$ of the patient at the time t by using $X(t)$; and
   deriving the muscle weight $W_{muscle}(t)$, which provides an assessment of fitness and training status of the patient, as the weight of a second compartment of the patient by using $ICV_{basic}(t)$ and $ICV(t)$.

52. The method according to claim 51 wherein $W_{muscle}(t)$ is derived by the relation $$W_{muscle}(t) = \frac{(ICV(t) - ICV_{basic}(t))(1 + \gamma)}{\lambda_{TBW\_muscle}},$$

where $\gamma$ is the ratio between the extracellular water to intracellular water volume in the second compartment and $\lambda TBW_{\_muscle}$ is the fraction of water per unit mass in the second compartment.

53. The method according to claim 51 wherein the weight $W_{basic}(t)$ of the first compartment of the patient at the time t is also derived by using $X(t)$.

54. The method according to claim 53 wherein a lean body mass $LBM(t)$ of the patient at the time t is derived by using the equation $$LBM(t) = W_{basic}(t) + W_{muscle}(t).$$

55. The method according to claim 51 wherein the first compartment comprises the skeleton, organs, blood and skin of the patient.

* * * * *